(12) United States Patent
Lobbert et al.

(10) Patent No.: US 9,488,581 B2
(45) Date of Patent: Nov. 8, 2016

(54) ARRANGEMENT FOR OPTICAL MEASUREMENT OF A PROCESS VARIABLE AND MEASURING DEVICE COMPRISING SUCH AN ARRANGEMENT

(71) Applicant: Endress + Hauser Conducta Gesellschaft für Mess- und Regeltechnik mbH + Co. KG, Gerlingen (DE)

(72) Inventors: Andreas Lobbert, Waldheim (DE); Ronny Michael, Erlau (DE); Christian Fanselow, Geringswalde (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 14/444,218

(22) Filed: Jul. 28, 2014

(65) Prior Publication Data

US 2015/0034807 A1  Feb. 5, 2015

(30) Foreign Application Priority Data

Jul. 31, 2013 (DE) .......................... 10 2013 108 189

(51) Int. Cl.
| | |
|---|---|
| *G01N 21/64* | (2006.01) |
| *G01J 1/44* | (2006.01) |
| *G01N 21/77* | (2006.01) |
| *G01J 1/04* | (2006.01) |
| *G01N 21/78* | (2006.01) |
| *G01N 21/80* | (2006.01) |

(52) U.S. Cl.
CPC .............. *G01N 21/645* (2013.01); *G01J 1/44* (2013.01); *G01N 21/77* (2013.01); *G01J 1/0425* (2013.01); *G01N 21/78* (2013.01); *G01N 21/783* (2013.01); *G01N 21/80* (2013.01); *G01N 2021/6432* (2013.01); *G01N 2021/6484* (2013.01);

(Continued)

(58) Field of Classification Search
CPC ................. G01N 21/63; G01N 21/64; G01N 2021/6484
USPC ............ 250/227.11, 227.14, 227.28, 227.29, 250/227.32, 458.1, 486.1
See application file for complete search history.

(56) References Cited

U.S. PATENT DOCUMENTS

| | | |
|---|---|---|
| 5,459,570 A | 10/1995 | Swanson |
| 5,647,368 A | 7/1997 | Zeng |

(Continued)

FOREIGN PATENT DOCUMENTS

| | | |
|---|---|---|
| CN | 101566507 A | 10/2009 |
| CN | 102103081 A | 6/2011 |

(Continued)

OTHER PUBLICATIONS

German Search Report, German PTO, Munich, Jun. 25, 2014.

*Primary Examiner* — Kevin Pyo
(74) *Attorney, Agent, or Firm* — Christopher R. Powers; PatServe

(57) ABSTRACT

An arrangement for optical measurement of at least one process variable in a medium, comprising: at least one light source; at least one light receiver; an optical sensor element at least one data processing unit; and a light conductor. The light conductor connects the light source with the optical sensor element and the optical sensor element with the light receiver. The light conductor is embodied with at least three arms, wherein the first arm is arranged at the light source, the second arm is arranged at the light receiver and the third arm is arranged at the optical sensor element first arm and the second arm combine to form the third arm. The invention relates further to a measuring device comprising an above described arrangement.

18 Claims, 2 Drawing Sheets

(52) U.S. Cl.
CPC ............ *G01N2021/7786* (2013.01); *G01N 2201/0826* (2013.01); *G01N 2201/0833* (2013.01)

(56) References Cited

U.S. PATENT DOCUMENTS

| | | | |
|---|---|---|---|
| 6,718,077 | B1 | 4/2004 | Ferreira |
| 6,899,675 | B2 | 5/2005 | Cline |
| 6,975,898 | B2 | 12/2005 | Seibel |
| 7,019,309 | B2 | 3/2006 | Gu |
| 7,190,457 | B2 | 3/2007 | Tabacco |
| 7,389,009 | B2 | 6/2008 | Iga |
| 7,417,238 | B2 * | 8/2008 | Lau .................... G01J 1/58 250/486.1 |
| 7,876,446 | B2 | 1/2011 | Korner et al. |
| 2006/0175555 | A1 | 8/2006 | Lau |
| 2009/0131800 | A1 | 5/2009 | Liang |
| 2012/0078075 | A1 | 3/2012 | Maynard |

FOREIGN PATENT DOCUMENTS

| | | |
|---|---|---|
| DE | 3518527 A1 | 11/1986 |
| DE | 37022210 A1 | 7/1987 |
| DE | 19857792 A1 | 7/2000 |
| DE | 19903506 A1 | 8/2000 |
| DE | 10218606 A1 | 11/2003 |
| DE | 102005061674 A1 | 7/2007 |
| DE | 102008011013 A1 | 9/2009 |
| DE | 69227902 T3 | 4/2010 |
| DE | 102011100507 A1 | 10/2012 |
| EP | 0940662 A1 | 2/1999 |
| EP | 1674854 A1 | 6/2006 |
| EP | 1846923 B1 | 10/2007 |
| EP | 0981735 B1 | 2/2008 |
| GB | 2126717 A | 3/1984 |
| GB | 2254417 A | 10/1992 |
| WO | 9852022 A1 | 11/1998 |
| WO | 0197902 A2 | 12/2001 |
| WO | 2010103999 A1 | 9/2010 |
| WO | 2012146398 A1 | 11/2012 |

* cited by examiner

ARRANGEMENT FOR OPTICAL MEASUREMENT OF A PROCESS VARIABLE AND MEASURING DEVICE COMPRISING SUCH AN ARRANGEMENT

TECHNICAL FIELD

The invention relates to an arrangement for optical measurement of a process variable, especially an analytical process variable, in a medium, as well as to a measuring device comprising such an arrangement.

BACKGROUND DISCUSSION

Although the invention will be explained in the following based on an oxygen sensor working according to the principle of fluorescence quenching, the inventive idea is not limited to such sensors. Rather, other process variables, especially concentrations of certain analytes, such as ions, molecules, gases or other chemical compounds, pH-value or temperature are likewise measurable by such an arrangement with corresponding modifications. Measuring devices suitable for determining such process variables are manufactured and sold by the group of firms, Endress+Hauser, in a large number of variants.

The sensor includes, for instance, a sensor head containing an optical sensor element. Adjoining the sensor head is a housing, which contains a data processing unit, wherein the optical sensor element is irradiated with light from a light source. The light, possibly after first being converted, is radiated back by the optical sensor element with a certain light characteristic, detected by a light receiver and a signal of the light receiver representing the light characteristic evaluated by the data processing unit.

Known from European Patent EP 2 295 953 A1 is a system for measuring substance concentrations in solutions based on a fluorescence measurement. The system includes a light source, which radiates light into a medium to be examined. This transmitted light excites an optical sensor element, which is arranged in contact with the medium to be examined. In the fluorescence measurement, the transmitted light is absorbed by the optical sensor element and light of another wavelength radiated back as a function of a process variable, thus, for instance, the concentration of an analyte. The radiation radiated back by the optical sensor element is absorbed by a light receiver as received light, converted into an electrical, measured variable and forwarded to a data processing unit. Depending on properties of the optical sensor element, the optical sensor reacts to different particle concentrations with different received light intensities, received frequencies, phase angle and/or decay curves.

Fundamentally, there are different methods for arranging the light source/light receiver relative to the optical sensor element, as is explained below.

In the case of sensors with sufficient energy supply, the light source/light receiver can be arranged directly at the optical sensor element. This is, however, difficult to implement in the case of high temperature sensors, since long and disturbance susceptible, connecting lines result between the optical components and the data processing unit arranged remotely from the high temperature measuring point.

In order to avoid this, light source and light receiver can be placed far from the possibly hot medium to be examined. Then the light can be brought to the optical sensor element via a single light conductor. This cannot be done for compact sensors characterized by small constructions, since a relatively large light conductor is required.

Additionally, separate light conductors can be used for light source and light receiver. This is known, for example, from European Patent EP 0 940 662 B1. For an optimal measurement signal, the light conductor must point at the optical sensor element at an angle of, for instance, 45°. This again cannot be implemented for compact sensors.

Described in German Patent DE 102 18 606 A1 is a digital sensor, which is composed of two components connected releasably with one another: A sensor-side component (plug head), with which a sensor element (there, a potentiometric sensor) and a data memory are inseparably connected, and a transmitter-side component (a pluggable connector coupling or a sensor cable), via which the sensor-side component is coupled with a measurement transmitter or directly with a control system. A digital, bidirectional data transfer between the two described sides occurs contactlessly via a magneto inductively coupling interface. Energy transfer via the contactless, magneto inductive interface occurs unidirectionally. Energy transmission via a galvanically separated interface provides comparatively little energy to the sensor side component. Corresponding sensors are manufactured and sold by the applicant under the mark "Memosens". The "Memosens" technology is applicable not only for potentiometric sensors, but, instead, in principle, for any sensor used for determining and monitoring the most varied of process variables.

SUMMARY OF THE INVENTION

An object of the invention is to provide optimal light input and light output for compact, optical, low energy sensors.

The object is achieved by an arrangement for optical measurement of a process variable, especially an analytical process variable, in a medium, comprising: at least one light source for transmitting light; at least one light receiver for receiving light, wherein the light receiver transduces received light into an electrical, measured variable; an optical sensor element, wherein the optical sensor element is located at least partially in contact with the medium and converts transmitted light into received light; and at least one data processing unit for operating and controlling the light source and/or for processing the electrical, measured variable into the process variable. The arrangement is characterized in that a light conductor is provided, wherein the light conductor connects the light source with the optical sensor element and the optical sensor element with the light receiver, wherein the light conductor is embodied with multiple arms and has a first arm, a second arm and a third arm, wherein the first arm is arranged at the light source in such a manner that transmitted light enters into the first arm, wherein the second arm is arranged at the light receiver in such a manner that received light enters from the second arm into the light receiver, wherein the third arm is arranged at the optical sensor element in such a manner that transmitted light from the third arm strikes the optical sensor element and received light from the optical sensor element enters into the third arm, and wherein the first arm and the second arm combine to form the third arm.

It thus becomes possible to locate the light source, for instance, an LED, and the light receiver, for instance, a photodiode, remotely from the possibly hot medium. In its simplest form, the light conductor has a Y shape. Through the application of a light conductor having a plurality of arms starting from the LED, respectively the photodiode, wherein the plurality of arms combine to form a single arm at the optical sensor element, it becomes possible to maximize light recovery.

In a first advantageous variant, the light conductor is embodied as a glass rod. This is a cost effective solution. In such case, the first and second arms of the glass rod are so bent that they join to form the third arm. As already mentioned, in such case, a Y shape can result, i.e. the glass rod is embodied as a glass rod branching at one end.

In a second advantageous variant, the light conductor is composed of a fiber bundle formed of a plurality of fibers, wherein a first group of fibers, the transmitting fibers, form the first arm, and wherein a second group of fibers, the receiving fibers, form the second arm. By applying flexible fibers, it then becomes possible to equalize length differences, which may occur. This problem is, for instance, manufacturing related or arises due to temperature fluctuations.

In an additional advantageous variant, the light conductor is composed of fiber bundles formed of a plurality of fibers, wherein, besides the already mentioned first and second groups of fibers, third and fourth groups of fibers are provided. The third, respectively fourth, group of fibers forms a fourth, respectively fifth, arm of the light conductor. Also, the fourth and fifth arms combine to help form the third arm. While the first arm sends transmitted light for a first process variable and the second arm receives received light for the first process variable, the fourth arm can send transmitted light for a second process variable, respectively the fifth arm receives received light for the second process variable. Examples of different process variables are, for instance, oxygen and temperature, however, also the already mentioned process variables.

In a first advantageous variant of the fiber arrangement, transmitting fibers and receiving fibers are so distributed in the third arm that in the cross section of the third arm the transmitting fibers form a first circle portion, and the receiving fibers a second circle portion, which completes the first circle portion, wherein the first circle portion has a smaller surface area than the second circle portion.

In a second advantageous variant of the fiber arrangement, the transmitting fibers and receiving fibers are distributed equally in the third arm.

In a third advantageous variant of the fiber arrangement, the receiving fibers form an inner circle and the transmitting fibers a coaxial, outer, circular ring around the inner circle.

In order to increase light recovery further and to reduce the number of light reflecting interfaces, preferably at least one optical filter and/or lens is provided in the light conductor, especially at the interface between light source and first arm, between light receiver and second arm, as well as between optical sensor element and third arm.

In an advantageous embodiment, the ends of the fibers of the light conductor facing the optical sensor element are cut off at an angle less than 90° to their longitudinal axes. Thus, it is further possible to maximize the light recovery, since the transmitted light strikes the optical sensor element at an angle and is received then, after conversion by the optical sensor element, as received light at an angle in the receiver.

In a preferred form of embodiment, the optical sensor element is embodied as a photoluminescence sensor, especially as a fluorescence sensor or phosphorescence sensor, wherein the optical sensor element, after excitation with the transmitted light, emits light as received light as a function of the process variable. The light received in the light receiver can be analyzed in different ways, and, thus, determined as a function of the process variable. Possible ways include evaluating differences in intensity, phase angle, response time, etc.

In an additional preferred form of embodiment, the optical sensor element includes at least one layer, which, in contact with the process variable, changes at least one property, especially changes color, and absorbs transmitted light as a function of the process variable.

Preferably, the light conductor is a light conductor having a numerical aperture greater than 0.1.

In a form of embodiment, the power consumption of the arrangement, especially of the light source and the data processing unit, in general, thus, the sensor electronics, is less than 1 W.

The object is further achieved by a measuring device comprising an above described arrangement, wherein the measuring device includes a sensor-side component and a transmitter-side component; wherein the arrangement is positioned on/in the sensor side component; wherein energy is transmitted unidirectionally from the transmitter-side component to the sensor side component and data, especially the electrical, measured variable and/or the process variable, are transmitted bidirectionally, and the sensor-side component and the transmitter-side component are coupled with one another via a galvanically isolated connection, especially an inductive connection, or the sensor-side component and the transmitter-side component are galvanically coupled and are connected with a control system via a galvanically isolated connection.

The measuring device is, for instance, a measuring device for a measured, process variable from the field of process automation, for instance, an analytical, process variable, for example, the concentration of an analyte, for example, oxygen concentration.

BRIEF DESCRIPTION OF THE DRAWINGS

The invention will now be explained in greater detail based on the drawing, the figures of which show as follows.

DETAILED DISCUSSION IN CONJUNCTION WITH THE DRAWINGS

Figure 1:
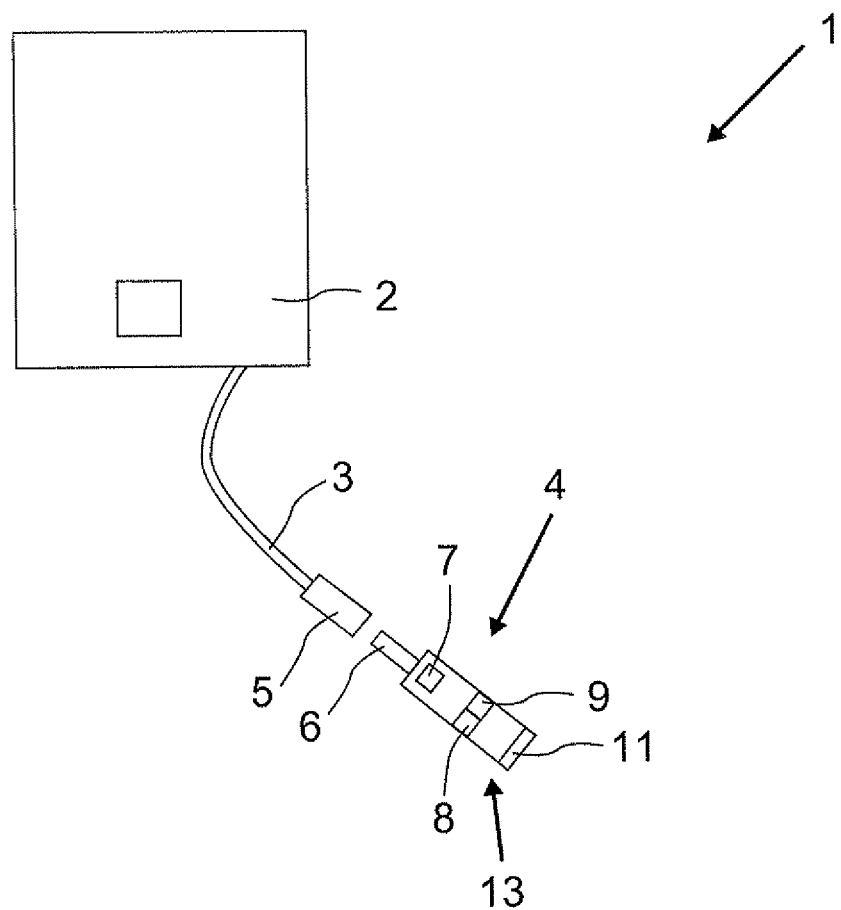
FIG. 1 is a measuring device of the invention.

In the figures, equal features are provided with equal reference characters.

First, the measuring device 1 of the invention will be explored. In such case, the measuring device 1 is not to be understood as a single component, but, instead, as a combination of a transmitter-side component and a sensor-side component. The transmitter-side component is, for instance, a superordinated unit 2, e.g. a transmitter or a control station. Superordinated unit 2 includes at least one data processing unit. The sensor-side component is a consumer, e.g. a sensor 4, connected via a cable 3. The connection between the superordinated unit 2 and the consumer occurs via interfaces 5, 6. Interfaces 5, 6 are embodied as galvanically isolated interfaces, especially inductive interfaces.

Sensor 4 is supplied with energy via cable 3. Furthermore, data are exchanged bidirectionally between sensor 4 and transmitter 2. A portion of the tasks of the transmitter 2 can be accomplished by preprocessing in the sensor 4, especially in a data processing unit 7, for instance, in a microcontroller. Stored in the microcontroller 7, respectively in its memory, are sensor-specific data, such as, for instance, name, serial number, date of manufacture, device data, calibration data, firmware version identification, manufacturer information, device driver information, sensor data, historical data, process data.

Evaluation of the measurement data of the sensor 4 is divided between transmitter 2 and sensor 4. A preprocessing of the measurement data of the sensor 4 happens in the data processing unit 7. Especially, the light source 8 and the light receiver 9 (see FIG. 2) are controlled by the microcontroller. In a form of embodiment, the mentioned tasks are also assumed by an additional microcontroller located in the cable.

Sensor 4 is a sensor of process automation, especially an optical sensor. Examples include, thus, for instance, a pH-, temperature-, pressure-, oxygen-, or carbon dioxide sensor; a sensor for determining number of cells and cell structures; a sensor for monitoring certain organic or metal compounds; and a sensor for determining concentration of a chemical substance, for example, a certain element or a certain compound.

Transmitter 2 is connected furthermore to a control system or it is itself part of a control system. In the latter case, the sensor 4 is thus directly connected to a control system, for instance, via HART, 4 . . . 20 mA, Profibus, ModBus, Ethernet, etc.

Alternatively, the sensor 4 can also include an integrated transmitter and, thus, make use of transmitter functions and, in given cases, be directly connected to a control system. Sensor and integrated transmitter are then coupled galvanically with one another. Galvanic isolation occurs then via connection to a control system.

Figure 2:
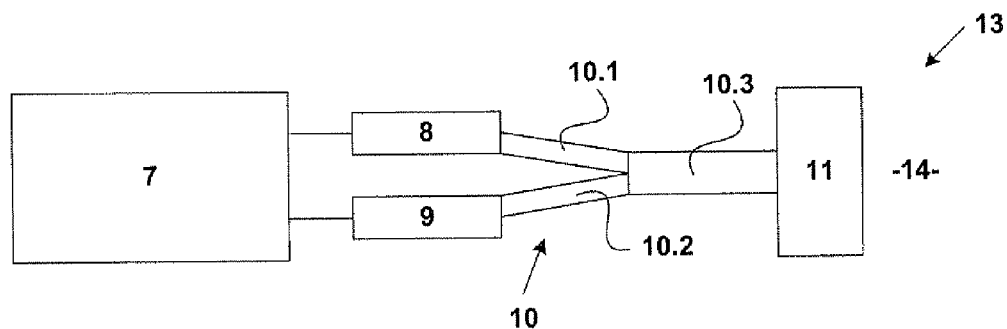
FIG. 2 is an arrangement according to the invention.

FIG. 2 shows an arrangement 13 of the invention in detail. Located on the right in FIG. 2 is an optical sensor element 11. Optical sensor element 11 is connected with a light source 8, respectively a light receiver 9, through a light conductor 10. Light source 8 and light receiver 9 are connected with the data processing unit 7. As already mentioned, light source 8 is operated by the data processing unit 7.

Light source 8 is, for instance, an LED; light receiver 9 is, for instance, a photodiode. As already mentioned, energy supply of arrangement 1 occurs via inductive interfaces 5, 6, via which no great energy densities are possible. Total energy consumption, respectively total converted power, of the arrangement 13, thus especially of data processing unit 7, light source 8 and light receiver 9, in general, thus, the sensor electronics, should, in such case, be below 1 W.

Connected with the light source 8 is a first arm 10.1 of the light conductor 10. Connected with the light receiver 9 is a second arm 10.2 of the light conductor 10. These connections are effected, for instance, by adhesive, joining or the like, wherein the particular method satisfies optical requirements such as, for instance, transparency at the corresponding wavelength, etc.

In an embodiment, an optical filter and/or a lens is provided at the interface between the light source 8 and the first arm 10.1, respectively between the light receiver 9 and the second arm 10.2, as well as at the interface between the third arm 10.3 and the optical sensor element 11 (see below).

First arm 10.1 and second arm 10.2 combine to form a third arm 10.3. Third arm 10.3 is connected with the optical sensor element 11 and the optical sensor element 11 is in contact with the medium 14.

Sensor 4 is embodied as an optical sensor, whose operation will now be briefly explained. Light source 8 sends transmitted light via the light conductors 10.1 and 10.3 to the optical sensor element 11. The optical sensor element 11 changes a property of the transmitted light and emits light to be received. Such received light takes a reverse path via the arms 10.3 and 10.2 to the light receiver 9. The property change involves, for instance, intensity, phase angle, wavelength, etc. Magnitude of the change depends in such case directly on the process variable to be measured in the medium, such as, for instance, the concentration of a certain analyte, for instance, oxygen concentration. The optical sensor element 11 is, thus, embodied as a fluorescent element or phosphorescent element.

As an alternative to the described fluorescence sensor, the optical sensor element 11 comprises at least one layer, which in the case of contact with the process variable in the medium 14 changes at least one property, i.e., for example, changes color, and absorbs transmitted light as a function of the process variable.

As already mentioned, sensor 4 is supplied with energy via an inductive interface 5, 6. As a result, only low amounts of energy are transmittable. The sensor usually has a diameter of 12 mm.

The arrangement in FIG. 2 can meet these energy and space constraints.

Light conductor 10 is embodied as a multi-arm, light conductor, in the example, as a two-arm, light conductor. The arms combine to a single arm on the sensor-side.

A possible embodiment of the light conductor 10 is implementation as a glass rod. The glass rod is formed, i.e. bent, drawn, etc., correspondingly. The two individual arms combine then to a single glass rod.

An alternative is to embody the light conductor 10 as a fiber bundle, wherein the fiber bundle is composed of a plurality of fibers. A first group of fibers, the transmitting fibers 12.1, form the first arm 10.1; a second group of fibers, the receiving fibers 12.2, form the second arm 10.2.

In a variant, the light conductor 10 includes besides the first arm 10.1 and the second arm 10.2, a fourth, respectively fifth, arm of the light conductor (these are not shown). Also, the fourth and fifth arms combine to form the third arm 10.3. While the first arm 10.1, as already mentioned, sends transmitted light for a first process variable and the second arm receives received light for the first process variable, the fourth arm permits sending transmitted light for a second process variable, respectively the fifth permits receiving received light for the second process variable. Examples of the different process variables are, for instance, oxygen and temperature.

It must be heeded that the region on the optical sensor element 11 covered by the receiving fibers 12.2 is also irradiated by the transmitting fibers 12.1.

The fibers are, for instance, fibers of adhered, joined or similarly formed glass fibers (air/glass), thick core fibers (quartz/quartz), polymer coated glass (air/polymer), plastic (POF-air/polymer) or photonic crystal fibers (glass/air, polymer/air).

On the side of the light conductor 10, respectively the third arm 10.3, facing the optical sensor element 11, the fibers can be differently arranged.

Figures 3A, 3B:
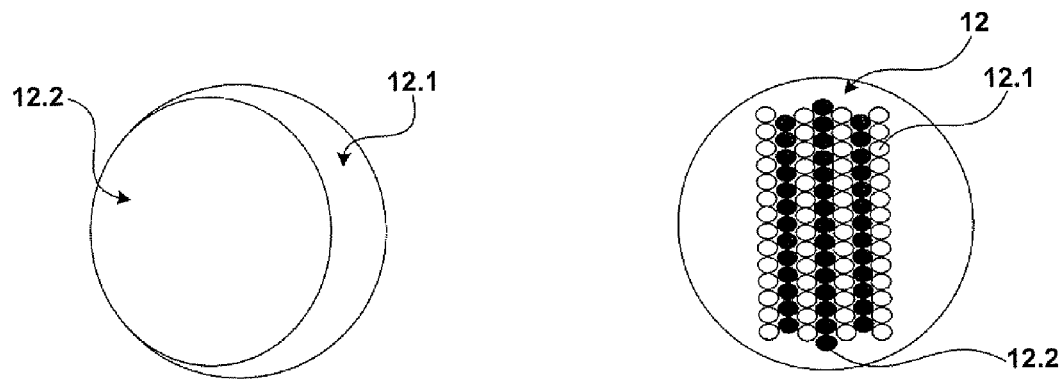
FIGS. 3a-3c are embodiments of the third arm of the light conductor in cross section.

FIG. 3 shows examples of different options. In FIG. 3*a*, the fibers are so distributed in the third arm 10.3 that in the cross section of the third arm 10.3 the transmitting fibers 12.1 form a first circle portion and the receiving fibers 12.2 a second circle portion, which completes the first circle portion. In an embodiment, the first circle portion is smaller in surface area than the second circle portion. Thus, a group of fibers can have, for instance, a "sickle", "half moon" or similar cross sectional form.

In FIG. 3b, the fibers 12.1, 12.2 are arranged equally distributed. In such case, for instance, a symmetry can result. Also, random distributions provide another option.

Figure 3C:
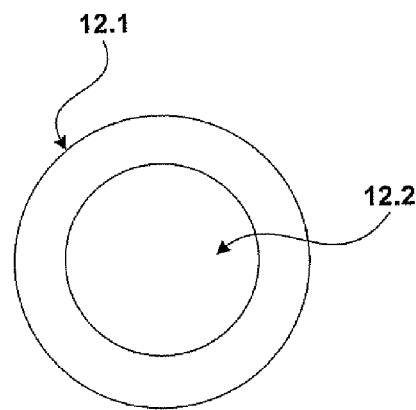

FIG. 3c shows an arrangement, in the case of which the receiving fibers 12.2 form an inner circle and the transmitting fibers 12.1 a coaxial, outer circular ring around the inner circle.

In order to increase light recovery, the ends of the fibers of the light conductor 10 facing the optical sensor element are cut off at an angle less than 90° to their longitudinal axes. This improves the guiding of the received and transmitted light.

In order to meet requirements for Ex protection, the arrangement 13 can, at least partially, be potted. In such case, especially a potting of the data processing unit 7 is beneficial.

The invention claimed is:

1. A measuring device, comprising:
at least one light source for transmitting light;
at least one light receiver for receiving light; said light receiver transduces received light into an electrical, measured variable;
an optical sensor element, said optical sensor element is located at least partially in contact with the medium and converts transmitted light into received light; and
at least one data processing unit for operating and controlling said at least one light source and/or for processing the electrical, measured variable into the process variable; and a light conductor, wherein:
said light conductor connects said at least one light source with said optical sensor element, and said optical sensor element with said light receiver;
said light conductor is embodied with at least three arms and has a first arm, a second arm and a third arm;
said first arm is arranged at said at least one light source in such a manner that transmitted light enters into said first arm;
said second arm is arranged at said light receiver in such a manner that received light from the second arm enters into said light receiver;
said third arm is arranged at said optical sensor element in such a manner that transmitted light from said third arm strikes the optical sensor element and received light from said optical sensor element enters into said third arm; and
said first arm and said second arm combine to form said third arm; wherein:
the measuring device includes a sensor-side component and a transmitter-side component;
the arrangement is positioned on/in said sensor-side component;
energy is transmitted unidirectionally from said transmitter-side component to said sensor-side component and data are transmitted bidirectionally;
said sensor-side component and said transmitter-side component are coupled with one another via a galvanically isolated connection or
said sensor-side component and said transmitter-side component are galvanically coupled and are connected with a control system via a galvanically isolated connection.

2. The measuring device as claimed in claim 1, wherein: said light conductor is embodied as a glass rod.

3. The measuring device as claimed in claim 1, wherein: said light conductor comprises a fiber bundle formed of a plurality of fibers;
a first group of fibers, the transmitting fibers, form said first arm; and
a second group of fibers, the receiving fibers, form said second arm.

4. The measuring device as claimed in claim 3, wherein: said transmitting fibers and receiving fibers are so distributed in said third arm that in the cross section of said third arm the transmitting fibers form a first circle portion, and the receiving fibers a second circle portion, which completes the first circle portion; and
said first circle portion has a smaller surface area than said second circle portion.

5. The measuring device claimed in claim 3, wherein: said transmitting fibers and receiving fibers are distributed equally in said third arm.

6. The measuring device as claimed in claim 3, wherein: said receiving fibers form an inner circle and said transmitting fibers a coaxial, outer, circular ring around said inner circle.

7. The measuring device as claimed in claim 1, further comprising:
at least one optical filter and/or lens in said light conductor.

8. The measuring device as claimed in claim 1, wherein: ends of the fibers of said light conductor facing said optical sensor element are cut off at an angle less than 90° to their longitudinal axes.

9. The measuring device as claimed in claim 1, wherein: said optical sensor element is embodied as a photoluminescence sensor; and
said optical sensor element, after excitation with the transmitted light, emits light as received light as a function of the process variable.

10. The measuring device as claimed in claim 1, wherein: said optical sensor element includes at least one layer, which, in contact with the process variable in the medium, changes at least one property and absorbs transmitted light as a function of the process variable.

11. The measuring device as claimed in claim 1, wherein: said light conductor is a light conductor having a numerical aperture greater than 0.1.

12. The measuring device as claimed in claim 1, wherein: power consumption of the measuring device is less than 1 W.

13. The measuring device as claimed in claim 1, wherein the electrical, measured variable and/or the process variable are transmitted bidirectionally.

14. The measuring device as claimed in claim 1, wherein the said galvanically isolated connection is an inductive connection.

15. The measuring device as claimed in claim 7, wherein said at least one optical filter and/or lens is disposed at interfaces between said light source and said first arm, between said light receiver and second arm, and/or between said optical sensor element and said third arm.

16. The measuring device as claimed in claim 9, wherein said photoluminescence sensor is a fluorescence sensor or a phosphorescence sensor.

17. The measuring device as claimed in claim 10, wherein said at least one property is color.

18. The measuring device as claimed in claim 1, wherein a power consumption of said light source and said data processing unit is less than 1 W.

* * * * *